United States Patent [19]

Nagasaki

[11] Patent Number: 4,633,304

[45] Date of Patent: Dec. 30, 1986

[54] ENDOSCOPE ASSEMBLY

[75] Inventor: Tatsuo Nagasaki, Musashino, Japan

[73] Assignee: Olympus Optical Co., Ltd., Tokyo, Japan

[21] Appl. No.: 644,421

[22] Filed: Aug. 27, 1984

[30] Foreign Application Priority Data

Aug. 27, 1983 [JP] Japan .................. 58-156859

[51] Int. Cl.⁴ .............................. H06N 7/18
[52] U.S. Cl. ......................... 358/98; 128/6; 128/903; 455/95
[58] Field of Search ............... 358/98; 128/903, 6; 455/95, 100

[56] References Cited

U.S. PATENT DOCUMENTS

| 3,374,787 | 3/1968 | Hatke | 455/100 |
| 3,651,405 | 3/1972 | Whitney | 455/129 |
| 3,986,498 | 10/1976 | Lewis | 128/903 |
| 3,993,861 | 11/1976 | Baer | 358/142 |
| 4,261,344 | 4/1981 | Moore | 358/98 |
| 4,412,244 | 10/1983 | Shanley | 358/183 |
| 4,535,758 | 8/1985 | Longacre | 128/6 |

Primary Examiner—Howard W. Britton

[57] ABSTRACT

The endoscope assembly of the present invention can transmit an imae formed by means of a pickup element of an object to be observed as image information. It is composed of signal conversion means for converting the output from the pickup element into image signals, modulation means for modulating the image signals, transmission means for transmitting the modulated image signals and means for illuminating said object so as to transmit the image information in a cavity of living or mechanical body as electrical wave to receive the image on a receiver.

5 Claims, 5 Drawing Figures

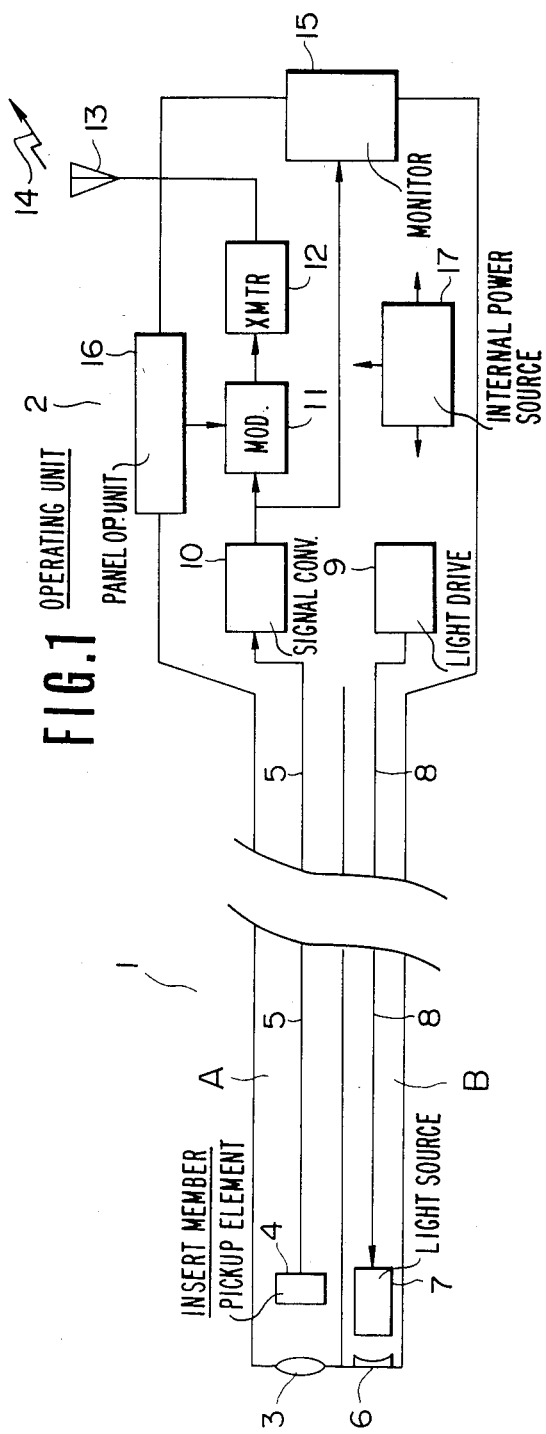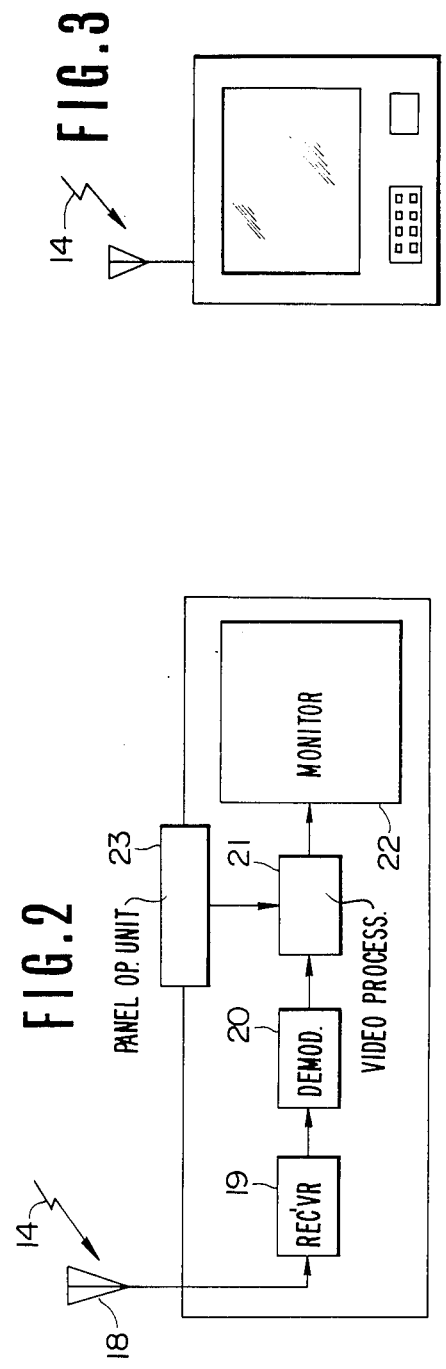

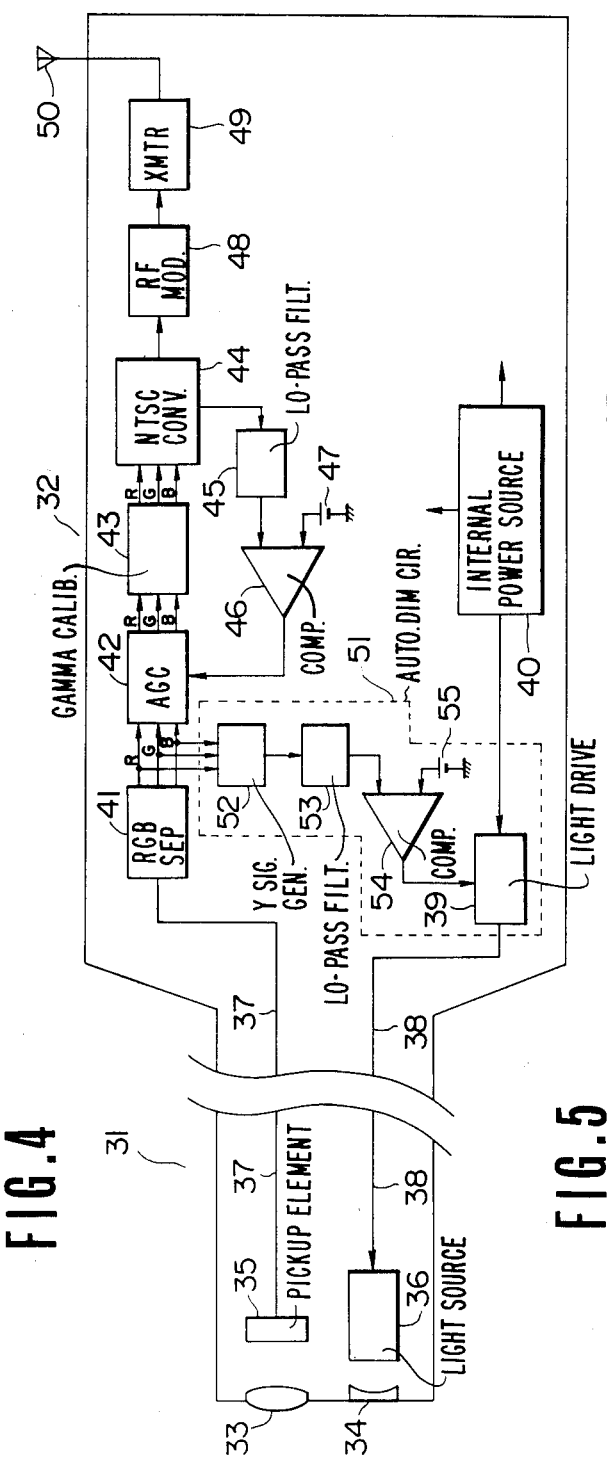
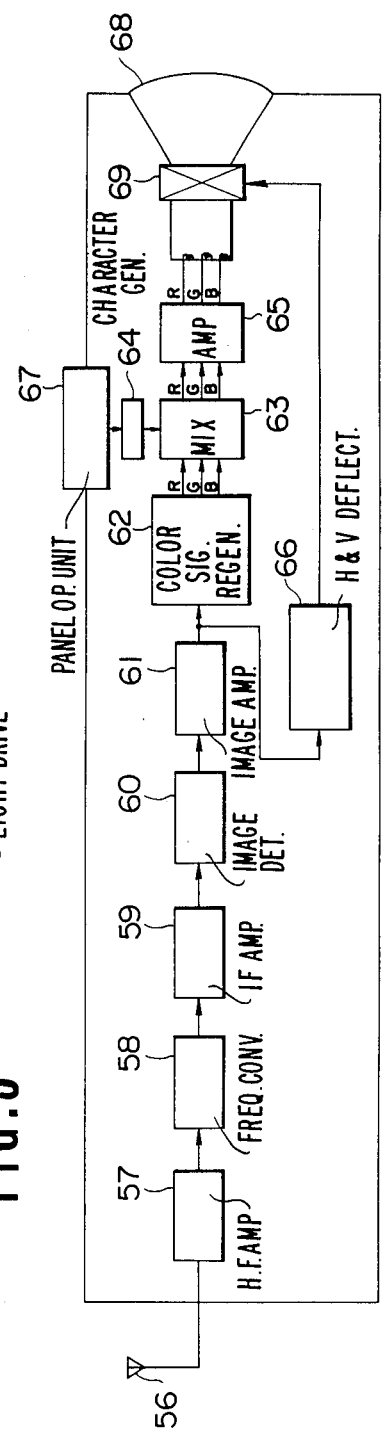
FIG.4
FIG.5

ENDOSCOPE ASSEMBLY

BACKGROUND OF THE INVENTION

The present invention relates to an endoscope assembly comprising a pickup element, a wireless transmitter for transmitting pictorial information picked up by means of said pickup elements in a body cavity or other cavity by means of electric wave and a display unit which receives the transmitted electric waves and visualizes the pictorial information.

An endoscope has been generally used for observing a cavity in a living body or a cavity of mechanical parts. By such an endoscope, an image of an object to be observed has been transmitted from the cavity of a living body or other body by means of optical fibre bundles and the optical image focussed on the output end of optical fibre bundle has been observed by means of an optical lens system. On the other hand, there has been developed a device wherein a pickup element such as a charge-coupled elements (referrred hereinafter as CCD) is installed at the tip of the shaft of endoscope in lieu of said optical fibre, the optical image formed on the receptor surface of this pickup element is converted into an electric signal, which is transmitted from the cavity of living body or mechanical body, processed at the outside of the cavity and displayed on a screen of a television. In such an endoscope, a light source unit is usually installed at the outside of cavity so that the light from the unit is guided through the connector means (light guide) of endoscope to the probe thereof to irradiate the object to be observed.

In the above-mentioned conventional endoscope assemblies, the former system for the optical observation is provided with the light guide for guiding illumination light for illuminating the object to be observed and the observation is carried out directly by the naked eye though an optical lens system so that the handling as well as the observation are not done easily. In the case of the observation of image employing the latter pickup element, the image of an object can be observed on a large-sized screen of a television but the assembly requires a light guide for illuminating the object to be observed in a similar manner to the former optical system, and a signal circuit for connecting the signal to the television, thus the system has a disadvantage that it is not handled easily.

BRIEF SUMMARY OF THE INVENTION

In view of the disadvantages as referred to hereinbefore, it is a major object of the present invention to provide an endoscope assembly wherein only a pickup element is used to send the pictorial information of an object to be observed to a separately installed television in the form of an electric wave and be displayed thereon. It is another object of the present invention to provide an endoscope assembly wherein no signal transmitting circuit nor light guide for guiding illuminating light into the endoscope is provided so that it may be handled easily and have high workability.

It is a further object of the present invention to provide a portable endoscope assembly.

Other features and objects will be understood clearly by the following description.

BRIEF DESCRIPTION OF THE DRAWINGS

FIG. 1 is a schematic view for illustrating an outlined structure of an endoscope assembly according to the present invention.

FIG. 2 is a schematic view for illustrating an outlined structure of a receiver.

FIG. 3 is a front view of a television receiver employed as a receiver.

FIG. 4 is a block diagram of an embodiment of circuits in the endoscope assembly.

FIG. 5 is a block diagram of an embodiment of receiver means.

DETAILED DESCRIPTION OF THE EMBODIMENTS

As shown in FIG. 1, the endoscope assembly is composed of an insert member 1 to be inserted into the cavity of a living body or mechanical body and an operating unit 2 physically connected to said insert member 1. The insert member 1 is composed of a metallic or flexible material and its inner portion is partitioned into two compartments A, B, compartment A being used for the picking-up and compartment B for the light source. The picking-up compartment A in the insert member 1 is provided with a pickup lens system 3 and a pickup element 4 such as a CCD for receiving the optical image incident through lens system 3 and converting the optical image into electric signals to be fed to the electric circuit in operating unit 2 through lead wires 5. The light source compartment B in the insert member 1 is provided with an irradiating lens system 6 at the tip thereof so that light is irradiated on the object to be observed from light source unit 7 provided at the back of lens system 6. Light source unit 7 is composed of a luminous diode or lamp connected to a light source driving unit 9 of operating unit 2 through lead wires 8. Operating unit 2 is equipped with said light source driving unit 9 and, in addition, a signal converter unit 10, modulator unit 11 and transmitter unit 12 so that the electric signals from pickup element 4 are converted into image signals through signal converter unit 10. The amplitude of high frequency current (AM) is modulated by the image signals issued from signal converter unit 10 through modulator unit 11 to be fed to transmitter unit 12 and electric carrier wave 14 is transmitted through antenna 13. In addition, signal converter unit 10 is connected with a small-sized monitor unit 15 such as liquid crystal monitor and modulator unit 11 is connected with a panel operating unit 16. Panel operating unit 16 is provided with a keyboard for inputting character (letter) signals, shutter releasing button and freezing button for displaying a stationary image by actuating the frame memory in the receiver unit. Said light source driving unit 9, signal converter unit 10, modulator unit 11, transmitter unit 12 and monitor unit 15 are connected to an internal power source 17 such as galvanic cells, etc. for driving these members. In addition, monitor unit 15 may be omitted and these unit may be actuated by means of an external power source in lieu of internal power source 17.

In the operation of such an endoscope assembly having the above mentioned structure, insert member 1 is inserted into the cavity of a living or mechanical body and pickup element 4 receives light from the object to be observed when the object is illuminated by light irradiated from light source unit 7. Signal converter unit 10 splits the light image received on pickup element 4 regularly and converts the light image subsequently into image signals so that the image is assembled conveniently on the receiver side and sends the image signals together with signals (synchronizing signals) representing the splitting condition to modulator unit 11. Modulator unit 11 adds or synthesizes the image signals with the signals from panel operating unit 16 and modulates the amplitude of the high frequency signals issued provisionally by the image signals. The modulated high frequency signals are amplified through transmitter unit 12 and transmitted from antenna 13 as an electric wave 14. The modulation mode of modulator unit 11 may be frequency modulation (FM) and the receiver should be structured so as to demodulate the frequency. In addition, the operational functions by panel operating unit 16 may be equipped only in the panel operator unit 23 in the receiver side as will be mentioned hereinafter.

Electric wave 14 sent as mentioned above are received by the receiver unit as shown in FIG. 2. The receiver means amplify selectively electric wave incident to antenna 18 through receiver unit 19 and demodulator 20 detects the amplitude modulation and demodulates the image signals to pickup the image signals as image signals formed by said signal converter unit 10. The image signals are applied through a video-processor 21 to a large-sized monitor unit 22 where the electric signals are converted again to optical signal to reproduce the optical image. Video-processor 21 is composed of frame memories for processing various signals and in order to reproduce the transmitted image by converting the image signals into an optical signal through monitor unit 22, the synchronizing signals sent together with the image signal are separated to control the deflection control tube of cathod ray tube and to synchronize the separation of the optical image performed at the transmitter side. In addition, video-processor 21 is connected with panel operating unit 23 arranged with a keyboard and buttons for effecting operations similar to said panel operating unit 16.

In addition, as the receiver unit as shown in FIG. 2 is incorporated with a large-sized monitor unit 22, it is inconvenient to be conveyed for employing it for various clinical uses. Hence, when the endoscope is to be used in a patient at his house, the image signals may be displayed employing a domestic television receiver as shown in FIG. 3 as a receiver, by setting the carrier frequency of television electric wave 14 so as to be displayed by actuating a blank channel of the television receiver.

The endoscope assembly according to the present invention sends image information employing a pickup element, signal converter unit, modulator unit and transmitter unit and a light guide may be installed in lieu of light source unit 7, lead wires 8 and light source driving unit 9 in FIG. 7 in a similar manner to a conventional endoscope to guide illuminating light from an external light source unit to the tip of insert member 1. FIGS. 4 and 5 illustrate a detailed structure of an embodiment of the endoscope assembly and receiver unit which are of the NTSC color television system and wherein the panel operating unit and monitor member are not arranged on the endoscope assembly side. The endoscope assembly is composed of an insert member 31 and operating unit 32 connected with the insert member. Insert member 31 is formed into a cylinder and a pickup lens system 33 and illuminating lens system 34 are equipped at the tip thereof. A pickup element 35 such as a CCD is attached at the rear of lens system 33 and a light source unit 36 such as an illuminating diode is attached at the rear of lens system 34. The electrical signals from pickup element 35 are transmitted through lead wire 37 to the electric circuit incorporated in operating unit 32. Pickup element 35 is composed of a mosaic color filter comprising red (R), green (G) and blue (B) arranged on the light receiving surface. On the other hand, light source unit 36 is connected to light source driving unit 39 incorporated in operating unit 32 through lead wire 38. Light source driving unit 39 is composed of a variable-current source constructed so that a current is supplied from internal power 40 which includes an accumulator such as galvanic cells and supplies DC voltage or DC current to every electric circuitry in the operating unit 32. Said lead wire 37 is connected to RGB separation circuitry 41, automatic gain control (AGC) circuitry 42 and gamma value calibration 43 and to or from NTSC signal converter unit 44. RGB separation circurtry 41 is composed of sample holding circuitry and separate R, G and B signals by sample holding the signals issued from pickup element 35 with sampling pulses. The separated R, G and B signals are subjected to automatic gain control through AGC circuitry 42. Gamma value calibration circuitry 43 is provided for calibrating provisionally the gamma value of an existing color television receiver and calibrates the R, G and B outputs from said circuitry 42 to input the calibrated outputs to the subsequent NTSC signal converter unit 44. NTSC signal converter unit 44 is provided with a matrix circuitry for preparing a brightness signal (Y-signal) and color difference signals (R-Y signal and B-Y signal) from the applied R, G and B signals and balanced modulation circuitry of the color difference signals to gain NTSC signal outputs comprising the balancedly modulated waves and Y-signals added with synchronizing signals. In addition, the Y-signals are picked up from the matrix circuitry in NTSC signal converter unit 44, passed through low-pass filter 45 and applied to one input terminal of a comparator 46. Comparator 46 is applied from another input terminal with a reference voltage from reference power source 47 and the compared output is applied to the AGC control terminal of said AGC circuitary 42 as the AGC voltage. The NTSC signals from NTSC signal converter unit 44 are supplied to RF modulator 48 in the modulator unit. RF modulator 48 AM modulates the high frequency carrier wave signal with the NTSC signals and the modulated output is passed through the subsequent transmitter unit 49 to transmitting antenna 50. Said light source driving unit 39 comprising the variable current source comprises a portion of automatic dimmer circuitry 51. Automatic dimmer circuitry 51 detect the R, G and B signals from RGB separation circuitry 41 to prepare Y-signals by inputting these signals to Y-signal generating circuitry 52 incorporated in the matrix circuitry. The Y-signals are passed through low-pass filter 53 to be applied to one input terminal of comparator 54. Another input terminal of comparator 54 is applied with a reference voltage from reference voltage source 55. The output from comparator 54 is supplied to the current controlling terminal of variable current source 39 to control automatically the driving current to be supplied to light source unit 36 from variable current source 39 depending on the magnitude of Y-signals so as to optimize the dosage illuminating the object to be observed.

FIG. 5 illustrates a receiver unit corresponding to the endoscope assembly as illustrated by FIG. 4. The modulated high frequency signals received by receiver antenna 56 are selected and intermediate frequency amplified through the receiver unit comprising high frequency amplifier circuitry 57, frequency converter circuitry 58 and intermediate frequency amplifier circuitry 59 to be fed to the subsequent demodifier unit. The demodifier unit is composed of image detector circuitry 60 and image amplifier circuitry 61 and detects the amplitude and amplifies the intermediate frequency signal to demodulate the NTSC signals. The demodulated NTSC signals are supplied to the video-processor unit, which comprises color signal regeneration crrcuitry 62, mixer circuitry 63, character generator unit 64, image amplifier circuitry 65 and synchronous deflector circuitry 66. Color signal regeneration circuitry 62 is composed of a demodulation circuitry for separating and demodulating the NTSC signals into Y-signals, R-Y signals and B-Y signals and a matrix circuitry for regenerating R, G and B signals from the demodulated Y-signals, R-Y signals and B-Y signals. The regenerated R, G and B signals are supplied to mixer circuitry 63 for compositing the R, G and B signal with character signals issued from character generator unit 64 connected to panel operating unit 67. Panel operating unit 67 is equipped a keyboard for the character signal input. The R, G and B signals passed through mixer circuitry 63 are amplified subsequent image amplifier circuitry 65 to be applied to the three axial cathodes of color television receiver 68. Synchronous deflector circuitry 66 separates the synchronous signals from the NTSC signals from image amplifier circuitry 61 to output the synchronous deflection signals to be applied to deflector coil 69 of color television receiver 68 to perform the horizontal and vertical deflection.

FIGS. 4 and 5 relate to the transmitter and receiver assemblies of standard NTSC color television system. It is also possible to design transmitter and receiver assemblies of PAL or SECAM color television system by replacing NTSC signal converter unit 44 and color signal regeneration circuitry 62 by circuits corresponding to the PAL or SECAM standard system.

It is obvious to design widely varied embodiments and modifications based on the present invention without departing from the spirit and scope of the present invention. Accordingly, the present invention should be restricted by the attached claims but not by any particular embodiments.

What is claimed is:

1. An endoscope assembly comprising:
    a flexible insert member adapted to be inserted into a body cavity and an operating unit physically connected to said insert member;
    said insert member including therewithin electrically energized illuminating means for illuminating an object to be observed and an image pickup element for receiving an optical image of said object and converting said optical image to electrical signals;
    connecting means in said insert member to electrically connect said image pick element and said illuminating means with said operating unit;
    said operating unit including therewithin signal conversion means connected to said connecting means for converting said image pickup element electrical signals to image signals, and modulating means connected to said signal converting means for modulating a carrier wave with said image signals; and
    transmitting means in said operating unit connected to said modulating means, including a transmitting antenna, for transmitting said image signals via said modulated carrier wave.

2. An endoscope assembly as recited in claim 1, further comprising in said operating unit an internal power source for providing power to said signal conversion means, said modulating means and said transmitting means and connected to said insert member for providing power to said illuminating means and said image pickup element.

3. An endoscope assembly as recited in claim 2, further comprising means for combining character signals with said image signals and feeding same to said modulating means for modulating said carrier wave to be transmitted by said transmitting means.

4. An endoscope assembly as recited in claim 2, further comprising in said operating unit a display means for receiving said image signals from said signal conversion means, converting said image signals to an optical image and displaying said optical image.

5. An endoscope assembly as recited in claim 2, further comprising in said operating unit a dimmer means for detecting the brightness level of said image signals at said signal conversion means, comparing said brightness level with a reference level, and adjusting the amount of light of said illuminating means based on the result of said comparison.

* * * * *